United States Patent [19]

Ollis et al.

[11] 4,410,523

[45] Oct. 18, 1983

[54] HETEROCYCLIC DERIVATIVES

[75] Inventors: William D. Ollis, Sheffield; Barry J. Price, Hertford; Linda Carey, Royston; Roger Hayes, Potters Bar; John W. Clitherow, Sawbridgeworth; John Bradshaw; John W. M. Mackinnon, both of Ware, all of England

[73] Assignee: Glaxo Group Limited, London, England

[21] Appl. No.: 199,522

[22] Filed: Oct. 22, 1980

[30] Foreign Application Priority Data

Oct. 22, 1979 [GB] United Kingdom .................. 7936544
Aug. 27, 1980 [GB] United Kingdom .................. 8027739

[51] Int. Cl.³ .................... A61K 31/395; C07D 249/10
[52] U.S. Cl. ............................... 424/246; 424/248.56; 424/263; 424/267; 424/269; 260/245.5; 544/60; 544/132; 546/210; 546/272; 548/265; 548/266; 548/267; 548/203; 548/214
[58] Field of Search ...................... 548/265, 266, 267; 546/210, 276; 544/132, 60; 260/245.5; 424/246, 248.56, 263, 267, 269

[56] References Cited

FOREIGN PATENT DOCUMENTS 1419994 1/1976 United Kingdom ................ 544/297
2003471 3/1979 United Kingdom ................ 546/210

Primary Examiner—Robert T. Bond
Attorney, Agent, or Firm—Bacon & Thomas

[57] ABSTRACT

The invention provides compounds of the general formula (I)

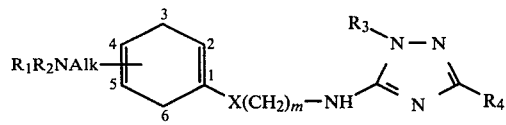

and physiologically acceptable salts, hydrates and bioprecursors thereof, in which $R_1$ and $R_2$, which may be the same or different, each represent hydrogen, $C_{1-10}$ alkyl, cycloalkyl, alkenyl, aralkyl, trifluoroalkyl, heteroaralkyl, or alkyl substituted by hydroxy, alkoxy, amino, alkylamino, dialkyamino or cycloalkyl, or $R_1$ and $R_2$ may together with the nitrogen atom to which they are attached form a 5 to 10 membered ring which may be saturated or may contain at least one double bond, may be unsubstituted or may be substituted by one or more $C_{1-3}$ alkyl groups, or a hydroxy group and/or may contain another heteroatom selected from oxygen and sulphur;

Alk represents a straight or branched alkylene chain of 1 to 6 carbon atoms and is attached to the cyclohexadiene ring at either the 4- or 5- position;

X represents $-CH_2$ or $-O-$;

m represents 2, 3, 4 or 5 and when X is $-O-$ the chain $(CH_2)_m$ may be interrupted by an oxygen atom provided that there are at least two methylene groups between any two heteroatoms in the moiety $-X(CH_2)_mNH-$;

$R_3$ represents hydrogen, alkyl, alkenyl, aralkyl, or $C_{2-6}$ alkyl substituted by hydroxy or alkoxy; and $R_4$ represents hydrogen, alkyl, alkenyl, aralkyl, hydroxyalkyl, acyloxyalkyl, alkoxyalkyl, aryloxyalkyl, aralkyloxyalkyl, aminoalkyl, alkylaminoalkyl, dialkylaminoalkyl, hydroxy or alkoxy or the group $NR_5R_6$ where $R_5$ represents hydrogen, alkyl, alkyl substituted by hydroxy or $C_{1-3}$ alkoxy, alkenyl, aralkyl or heteroaralkyl and $R_6$ represents any of the groups defined for $R_5$ or may represent the group $COR_7$ where $R_7$ represents hydrogen, alkyl, aryl, aralkyl, alkoxy, heteroaryl or monocyclic heteroaralkyl or $R_6$ represents the group $SO_2R_8$ where $R_8$ represents alkyl or aryl, or $R_6$ represents the group

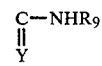

where Y is oxygen or sulphur and $R_9$ represents hydrogen, alkyl, cycloalkyl, aryl or aralkyl, or $R_5$ and $R_6$ taken together may represent the group $=CR_{10}R_{11}$ where $R_{10}$ represents aryl or heteroaryl and $R_{11}$ represents hydrogen or alkyl.

The compounds show activity as selective histamine $H_2$-antagonists.

9 Claims, No Drawings

HETEROCYCLIC DERIVATIVES

This invention relates to novel heterocyclic derivatives having action on histamine receptors, to processes for the preparation thereof, to pharmaceutical compositions containing them and to their use in therapeutics.

Certain novel heterocyclic derivatives have now been found which have potent activity as $H_2$-antagonists. These compounds, which are more particularly described below, for example show inhibition of the secretion of gastric acid when this is stimulated via histamine receptors (Ash and Schild, Brit. J. Pharmacol. Chemother, 1966, 27 427). This ability to do so can be demonstrated in the perfused rat stomach using the method described in German Offenlengungsschrift No. 2,734,070, modified by the use of sodium pentobarbitone (50 mg/kg) as anaesthetic instead of urethane, and in conscious dogs equipped with Heidenhain pouches using the method described by Black et al, Nature 1972 236, 385. Furthermore the compounds antagonise the effect of histamine on the contraction frequency of isolated guinea pig right atrium but do not modify histamine induced contractions of isolated gastro-intestinal smooth muscle which are mediated via $H_1$-receptors.

Compounds with histamine $H_2$-blocking activity may be used in the treatment of conditions where there is an advantage in lowering gastric acidity particularly in gastric and peptic ulceration, as a prophylactic measure in surgical procedures, and in the treatment of allergic and inflammatory conditions where histamine is a known mediator. Thus they may be used for example, either alone, or in combination with other active ingredients in the treatment of allergic and inflammatory conditions of the skin.

The present invention provides compounds of the general formula (I)

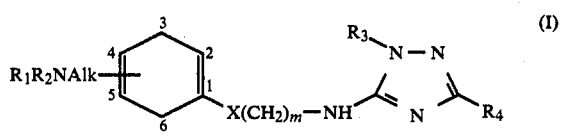

and physiologically acceptable salts, hydrates and bioprecursors thereof, in which $R_1$ and $R_2$, which may be the same or different, each represent hydrogen, $C_{1-10}$ alkyl, cycloalkyl, alkenyl, aralkyl, trifluoroalkyl, heteroaralkyl, or alkyl substituted by hydroxy, alkoxy, amino, alkylamino, dialkylamino or cycloalkyl, or $R_1$ and $R_2$ may together with the nitrogen atom to which they are attached form a 5 to 10 membered ring which may be saturated or may contain at least one double bond, may be unsubstituted or may be substituted by one or more $C_{1-3}$ alkyl groups, e.g. methyl, or a hydroxy group and/or may contain another heteroatom, e.g. oxygen or sulphur;

Alk represents a straight or branched alkylene chain of 1 to 6 carbon atoms preferably 1 to 4 carbon atoms, and is attached to the cyclohexadiene ring at either the 4 or 5-position;

X represents —$CH_2$— or —O—; m represents 2, 3, 4 or 5 and when X is —O— the chain $(CH_2)_m$ may be interrupted by an oxygen atom provided that there are at least two methylene groups between any two heteroatoms in the moiety —$X(CH_2)_mNH$—;

$R_3$ represents hydrogen, alkyl, alkenyl, aralkyl, or $C_{2-6}$ alkyl substituted by hydroxy or alkoxy; and $R_4$ represents hydrogen, alkyl, alkenyl, aralkyl, hydroxyalkyl, acyloxyalkyl, alkoxyalkyl, aryloxyalkyl, aralkyloxyalkyl, aminoalkyl, alkylaminoalkyl, dialkylaminoalkyl, hydroxy or alkoxy or the group $NR_5R_6$ where $R_5$ represents hydrogen, alkyl, alkyl substituted by hydroxy or $C_{1-3}$ alkoxy, alkenyl, aralkyl or heteroaralkyl and $R_6$ represents any of the groups defined for $R_5$ or may represent the group $COR_7$ where $R_7$ represents hydrogen, alkyl, aryl, aralkyl, alkoxy, heteroaryl or monocyclic heteroaralkyl or $R_6$ represents the group $SO_2R_8$ where $R_8$ represents alkyl or aryl, or $R_6$ represents the group

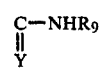

where Y is oxygen or sulphur and $R_9$ represents hydrogen, alkyl, cycloalkyl, aryl or aralkyl, or $R_5$ and $R_6$ taken together may represent the group =$CR_{10}R_{11}$ where $R_{10}$ represents aryl or heteroaryl and $R_{11}$ represents hydrogen or alkyl.

The term "alkyl" as a group or part of a group means that the group is straight or branched and has unless otherwise stated preferably 1 to 6 carbon atoms and in particular 1 to 4 carbon atoms e.g. methyl or ethyl and the term 'alkenyl' means that the group has preferably 3 to 6 carbon atoms. The term "cycloalkyl" means that the group has 3 to 8 carbon atoms. The term "aryl" as a group or part of a group preferably means phenyl or substituted phenyl, for example phenyl substituted with one or more $C_{1-3}$ alkyl or $C_{1-3}$ alkoxy groups or halogen atoms e.g. fluorine. The acyl portion of an acyloxyalkyl group means an aroyl, aralkanoyl or $C_{1-6}$ alkanoyl group. Examples of acyloxyalkyl groups include acetoxymethyl, formyloxymethyl, benzoyloxymethyl and phenylacetoxymethyl. The term "heteroaralkyl" within the definition of $R_1$ and $R_2$ means a group that is made up of a heteroaryl portion which is a 5-membered unsaturated ring e.g. furan or pyrrole, and a straight or branched $C_{1-4}$ alkyl portion; the heteroaryl ring is linked to the alkyl portion through either a carbon or nitrogen atom. The term "heteroaryl" within the definition of $R_4$ means a 5- or 6-membered monocyclic unsaturated ring which may contain one or more heteroatoms selected from oxygen, nitrogen and sulphur, e.g. furyl, pyridyl, thiazolyl and thienyl.

The invention includes the compounds of formula (I) in the form of physiologically acceptable salts with inorganic and organic acids. Particularly useful salts include hydrochlorides, hydrobromides, sulphates, methanesulphonates, acetates, maleates, succinates, citrates, tartrates, benzoates and fumarates. The compounds of formula (I) and their salts may also form hydrates, which hydrates are also to be considered as part of the invention. The compounds of formula (I) can exhibit tautomerism and the formula is intended to cover all tautomers. Where optical isomers may exist the formula is intended to cover all diastereoisomers and optical enantiomers. The term bioprecursors as used herein means compounds which have a structure different to that of the compounds of formula (I) but which, upon administration to an animal or human being, are converted in the body into a compound of formula (I).

The compounds according to the invention, preferably in the form of a salt, may be formulated for administration in any convenient way and the invention includes within its scope pharmaceutical compositions containing at least one compound according to the invention adapted for use in human or veterinary medicine. Such compositions may be formulated in a conventional manner using one or more pharmaceutically acceptable carriers or excipients. Such compositions may also contain if required other active ingredients, e.g. $H_1$-antagonists.

Thus the compounds according to the invention may be formulated for oral, buccal, topical, parenteral or rectal administration. Oral administration is preferred.

For oral administration, the pharmaceutical composition may take the form of for example, tablets, capsules, powders, solutions, syrups or suspensions prepared by conventional means with acceptable excipients. For buccal administration the composition may take the form of tablets or lozenges formulated in conventional manner.

The compounds of the invention may be formulated for parenteral administration by bolus injection or continuous infusion. Formulations for injection may be presented in unit dosage form in ampoules, or in multi-dose containers, with an added preservative. The compositions may take such forms as suspensions, solutions or emulsions in oily or aqueous vehicles and may contain formulatory agents such as suspending, stabilising and/or dispersing agents. Alternatively the active ingredient may be in powder form for reconstitution with a suitable vehicle, e.g. sterile pyrogen-free water before use.

The compounds of the invention may also be formulated in rectal compositions such as suppositories or retention enemas, e.g. containing conventional suppository bases such as cocoa butter or other glyceride.

For topical application, the compounds of the invention may be formulated as ointments, creams, gels, lotions, powders or sprays in a conventional manner.

For internal administration a convenient daily dosage regime of the compounds according to the invention would be 1 to 4 doses to the total of some 100 mg to 2 g per day, preferably 100 mg to 1 g per day, dependent upon the condition of the patient.

Examples of suitable meanings for the groups $R_1$ to $R_4$ are as follows:

$R_1$: alkyl (e.g. methyl, ethyl, propyl, butyl, isobutyl, pentyl, hexyl, heptyl or decyl), $C_{5-7}$ cycloalkyl (e.g. cyclopentyl, cyclohexyl or cycloheptyl), alkenyl (e.g. allyl or 3,3-dimethylallyl), aralkyl (e.g. phenylalkyl such as benzyl or phenethyl), $C_{1-4}$ alkyl substituted by a trifluoromethyl group (e.g. 2,2,2-trifluoroethyl), hydroxy $C_{2-4}$ alkyl (e.g. 3-hydroxypropyl), $C_{1-3}$ alkoxy $C_{2-4}$ alkyl (e.g. methoxyethyl or ethoxyethyl) or di-$C_{1-3}$ alkylaminoalkyl (e.g. dimethylaminoethyl, diethylaminoethyl or dimethylaminopropyl);

$R_2$: hydrogen or $C_{1-4}$ alkyl (e.g. methyl or ethyl); or $R_1R_2N$ may represent a 5–8 membered ring optionally containing one double bond and/or substituted by one or two $C_{1-3}$ alkyl (e.g. methyl) groups or a hydroxy group and/or containing an oxygen or sulphur atom (e.g. pyrrolidino, piperidino, hexamethylenimino, heptamethylenimino, tetrahydropyridino, 4-hydroxypiperidino, 4-$C_{1-3}$ alkylpiperidino (e.g. 4-methylpiperidino), morpholino, 2,6-di-$C_{1-3}$ alkylmorpholino (e.g. 2,6-dimethylmorpholino), or thiomorpholino;

$R_3$: hydrogen, $C_{1-4}$ alkyl (e.g. methyl, ethyl or propyl), or hydroxy $C_{2-4}$ alkyl (e.g. 2-hydroxyethyl);

$R_4$: hydrogen, hydroxy, $C_{1-4}$ alkyl (e.g. methyl, ethyl, or isobutyl), hydroxy $C_{1-4}$ alkyl (e.g. hydroxymethyl, 2-hydroxyethyl or 1-hydroxy-1-methylethyl), $C_{1-3}$ alkoxy $C_{1-4}$ alkyl (e.g. methoxymethyl or methoxyethyl), phenyl $C_{1-3}$ alkyl, (e.g. benzyl or phenethyl), $C_{2-4}$ alkanoyloxy $C_{1-4}$ alkyl (e.g. acetoxymethyl), amino $C_{1-4}$ alkyl (e.g. aminomethyl), amino, $C_{1-4}$ alkylamino (e.g. methylamino or ethylamino) or di-$C_{1-4}$ alkylamino (e.g. dimethylamino, diethylamino or dipropylamino), phenyl $C_{1-3}$ alkylamino (e.g. benzylamino), or a heteroaryl $C_{1-3}$ alkylamino group where the heteroaryl ring is 5 or 6 membered and contains one heteroatom (e.g. 3- or 4-pyridylmethyl); or the group $NHCOR_7$ where $R_7$ represents hydrogen, $C_{1-3}$ alkyl (e.g. methyl or ethyl), $C_{1-3}$ alkoxy (e.g. methoxy or ethoxy), furyl, pyridyl, thiazolyl, thienyl, or phenyl optionally substituted by a $C_{1-3}$ alkyl (e.g. methyl) or $C_{1-3}$ alkoxy (e.g. methoxy) group; or the group $NHSO_2R_8$ where $R_8$ represents $C_{1-3}$ alkyl (e.g. methyl), or phenyl optionally substituted by a $C_{1-3}$ alkyl (e.g. methyl) or $C_{1-3}$ alkoxy (e.g. methoxy) group; or the group $NHCONHR_9$ where $R_9$ is $C_{1-3}$ alkyl (e.g. methyl), $C_{5-7}$ cycloalkyl (e.g. cyclohexyl), or phenyl optionally substituted by a $C_{1-3}$ alkyl (e.g. methyl) or $C_{1-3}$ alkoxy (e.g. methoxy) group; or the group $N=CHR_{10}$ where $R_{10}$ is a phenyl or pyridyl (e.g. 3- or 4-pyridyl) group.

In particular the groups $R_1$ to $R_4$ may have meanings as follows:

$R_1$: $C_{1-7}$ alkyl (e.g. methyl, propyl, butyl, isobutyl or heptyl), $C_{1-4}$ alkyl substituted by a trifluoromethyl group (e.g. 2,2,2-trifluoroethyl), $C_{2-4}$ alkyl substituted by hydroxy or a di-$C_{1-3}$ alkylamino group (e.g. 3-hydroxypropyl or 2-dimethylaminoethyl), $C_{5-7}$ cycloalkyl (e.g. cyclohexyl), alkenyl (e.g. allyl), or phenyl $C_{1-3}$ alkyl (e.g. benzyl);

$R_2$: hydrogen or methyl or $R_1R_2N$ may represent a 5 to 7 membered ring optionally containing a double bond or an alkyl (e.g. methyl) substituent (e.g. piperidino 4-methylpiperidino, pyrrolidino, or hexamethylenimino or tetrahydropyridino);

$R_3$ hydrogen, methyl, ethyl or 2-hydroxyethyl;

$R_4$ hydroxy, phenyl $C_{1-3}$ alkyl (e.g. benzyl), $C_{1-4}$ alkyl substituted by hydroxy, $C_{1-3}$ alkoxy, $C_{2-4}$ alkanoyloxy or amino (e.g. hydroxymethyl, 2-hydroxyethyl, acetoxymethyl or aminomethyl); amino, di-$C_{1-4}$ alkylamino (e.g. diethylamino), $NHCOR_7$ where $R_7$ represents hydrogen, methyl, $C_{1-3}$ alkoxy (e.g. ethoxy) or phenyl, $NHCONHR_9$ where $R_9$ represents phenyl, or $N=CHR_{10}$ where $R_{10}$ is phenyl or pyridyl (e.g. 4-pyridyl).

The group Alk may be for example the group $(CH_2)_n$ where n is 1, 2 or 3, and is in particular a methylene or ethylene group, more particularly methylene.

The group $R_1R_2NAlk$ is preferably attached at the 5-position of the cyclohexadiene ring. X is preferably oxygen. m is preferably 3 or 4, more preferably 3.

A preferred group of compounds of formula (I) are those of formula (II)

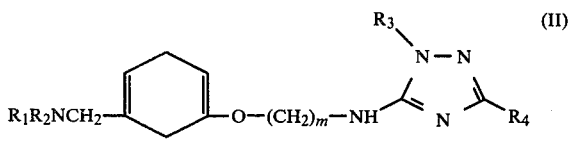

(II)

where $R_1$ and $R_2$ are methyl groups or together with the nitrogen atom to which they are attached form a pyrrolidino, piperidino or hexamethylenimino group; m is 3 or 4, $R_3$ is hydrogen or methyl; and $R_4$ is an amino, hydroxyalkyl, alkanoyloxyalkyl, alkoxyalkyl, aminoalkyl, benzyl, formamido, alkoxycarbonylamino, hydroxy, aroylamino or phenylcarbamoylamino group; $R_4$ may also represent amino, alkanoylamino, hydroxyalkyl, benzyl or pyridylmethylenamino.

Particularly preferred compounds are 1-methyl-$N^5$-[3-[[5-(1-piperidinylmethyl)-1,4-cyclohexadien-1-yl]oxy]propyl]-1H-1,2,4-triazole-3,5-diamine; and 1-methyl-5-[[3-[[5-(1-piperidinylmethyl)-1,4-cyclohexadien-1-yl]oxy]propyl]amino]-1H-1,2,4-triazole-3-methanol and their physiologically acceptable salts.

According to one aspect the invention provides compounds of formula (I) in which m represents 2, 3 or 4 and $R_4$ represents hydrogen, alkyl, alkenyl, aralkyl, hydroxyalkyl, alkoxyalkyl, hydroxy or alkoxy or the group $NR_5R_6$ where $R_5$ represents hydrogen, alkyl, hydroxyalkyl, alkenyl, or aralkyl and $R_6$ represents hydrogen, alkyl or hydroxyalkyl or $COR_7$ where $R_7$ represents hydrogen, alkyl, aryl, aralkyl or alkoxy, or $R_6$ represents the group $SO_2R_8$ where $R_8$ represents alkyl or aryl, or $R_5$ and $R_6$ together represent the group $=CR_{10}R_{11}$ where $R_{10}$ represents aryl or heteroaryl and $R_{11}$ represents hydrogen or alkyl.

It will be appreciated in the methods for the preparation of compounds of formula (I) given below, that for certain reaction steps it may be necessary to protect various reactive substituents in the starting materials for a particular reaction and subsequently to remove the protecting group. Such protection and subsequent deprotection may be particularly pertinent where $R_1$ and $R_2$ in intermediates used to prepare compounds of formula (I) are hydrogen atoms. Standard protection and deprotection procedures can be employed for example formation of a phthalimide group which may be cleaved by treatment with a hydrazine e.g. hydrazine hydrate or a primary amine for example methylamine.

In describing the processes which may be used for preparing the compounds of formula (I) or intermediates used in the preparation thereof, any of $R_1$ to $R_4$, Alk, X and m in the various formulae are as defined in formula (I) unless otherwise stated.

Compounds of formula (I), except when $R_4$ represents an acyloxyalkyl group or the group $-N=CR_{10}R_{11}$ can be prepared by a Birch reduction of compounds of formula (III)

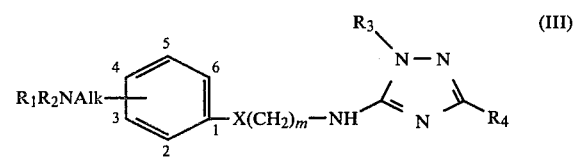

(III)

in which $R_4$ is other than acyloxyalkyl.

The reaction is carried out using an alkali metal, e.g. sodium, in liquid ammonia in the presence of an alcohol, e.g. absolute ethanol, at a temperature of from $-60°$ C. to $-33°$ C.

Under the conditions of the Birch reduction formation of a product of formula (I) may be accompanied by the formation of a small quantity of an isomeric cyclohexadienyl material. For example, reduction of a compound of formula (III) wherein the group $R_1R_2NAlk$ is in the 3-position gives the 1,4-cyclohexadiene derivative of formula (I) wherein the group $R_1R_2NAlk$ is in the 5-position and a small amount of the 1,4-cyclohexadiene derivative wherein the group $R_1R_2NAlk-$ is in the 3-position. The isomers may be separated if necessary and/or desired by conventional techniques.

Compounds of formula (I) in which $R_4$ represents the group $N=CR_{10}R_{11}$ may be prepared from compounds of formula (I) in which $R_4$ represents $NH_2$ by reaction with an aldehyde or ketone $R_{10}R_{11}CO$ in a solvent such as benzene, ethanol or methanol. The reaction is preferably carried out with heating, e.g. at reflux.

Compounds of formula (I) in which $R_4$ is an acyloxyalkyl group may be prepared by treating the corresponding hydroxyalkyl compound with an activated derivative of an appropriate acid, e.g. an acid chloride such as acetyl chloride in the presence of a base. e.g. pyridine.

Compounds of formula (I) in which $R_4$ is the group $NR_5R_6$ where $R_6$ is $-COR_7$, $-SO_2R_8$ or $-C(=Y)NHR_9$ may be prepared by treating an amino triazole (IV)

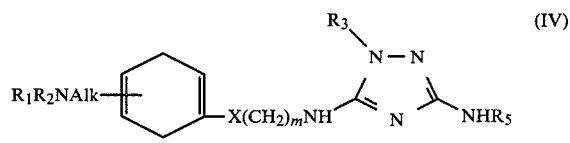

(IV)

in which $R_1$, $R_2$, $R_3$ and $R_5$ are as defined in formula (I) or are groups readily convertible thereto with a reagent capable of replacing the hydrogen atom in the group $NHR_5$ by the group $R_6$ where $R_6$ is as defined in formula (I).

Thus for example the aminotriazole (IV) may be reacted with an activated derivative of either a carboxylic acid $R_7COOH$ or a sulphonic acid $R_8SO_3H$ or the aminotriazole (IV) may be reacted with an isocyanate or isothiocyanate $R'_9NCY$ in which $R'_9$ has any of the meanings defined for $R_9$ in formula (I) except hydrogen or represents an alkali metal atom such as potassium or sodium or an alkoxycarbonyl group, e.g. ethoxycarbonyl, to give a compound of formula (I) in which $R_6$ is respectively the group $COR_7$, $SO_2R_8$ or

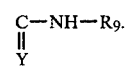

Suitable activated derivatives include acid halides e.g. acid chlorides, alkylchloroformates, acid anhydrides including mixed anhydrides (e.g. acetic formic anhydride), or esters such as alkyl esters, ortho esters and (1-alkyl-2-pyridinyl) esters.

The reaction with an acid halide is preferably carried out in the presence of a base e.g. an inorganic base such as sodium hydroxide or an organic base such as triethylamine or pyridine. The reaction with an alkylchloroformate is preferably carried out in the presence of a base, e.g. potassium carbonate or triethylamine, in a solvent such as dimethylformamide. The reaction with an acid anhydride may be carried out in the absence or presence of solvent such as pyridine.

In the reaction with an isocyanate or isothiocyanate compounds of formula (I) in which $R_9$ is other than hydrogen are conveniently prepared by carrying out the reaction in a solvent such as acetonitrile at an elevated temperature, e.g. reflux. Compounds of formula (I) in which $R_9$ is hydrogen may be prepared by heating the aminotriazole (IV) with an appropriate organic isocyanate or isothiocyanate such as ethylcarbonisothiocyanatidate, at an elevated temperature followed by hydrolysis of the resulting ester, for example with a base such as aqueous ethanolic sodium hydroxide.

Intermediates of formula (III) may in general be prepared by the methods described in British Patent specification No. 2023133A and in European Patent specification publication No. 0016565, or by processes analogous to these methods.

Where the product of any of the above processes is a free base and a salt is required, the salt may be formed in a conventional manner. Thus, for example, a generally convenient method of forming the salts is to mix appropriate quantities of the free base and the acid in an appropriate solvent(s), e.g. an alcohol such as ethanol or an ester such as ethyl acetate.

The invention is illustrated but not limited by the following examples.

In the following examples temperatures are in C. "T.l.c." refers to thin layer chromatography carried out on silica using, unless otherwise stated, one of the following solvent systems:

| System A | methanol:0.88 ammonia (80:1) |
|---|---|
| System B | ethyl acetate:water:isopropanol: 0.88 ammonia (25:8:15:2) |

EXAMPLE 1

(a) 1-methyl-$N^5$-[3-[[5-(1-piperidinylmethyl)-1,4-cyclohexadien-1-yl]oxy]propyl]-1H-1,2,4-triazole-3,5-diamine.

Ammonia gas was condensed onto a solution of 1-methyl-$N^5$-[3-[3-(1-piperidinyl-methyl)phenoxy]-propyl]-1H-1,2,4-triazole-3,5-diamine (1.0 g) in absolute ethanol (0.67 g) to give a total volume of 30 ml. Sodium (0.35 g) was added in small lumps such that the blue colour remained for almost 1 min before dispersing. The mixture was allowed to reflux during 0.5 h before adding ammonium chloride (1.0 g). The ammonia was allowed to evaporate at 20° and the white residue triturated with ethyl acetate (3×50 ml) and filtered through diatomaceous earth. The filtrate was evaporated to leave a colourless oil which was crystallised by trituration under cyclohexane (30 ml) and recrystallised from a mixture of ethyl acetate (20 ml) and cyclohexane (30 ml) to give a crude white crystalline solid (0.41 g) m.p. 99°–101°.

The crude product was partitioned between chloroform (25 ml) and water (25 ml). The chloroform layer was dried (MgSO$_4$), filtered and evaporated. The solid residue was crystallised from a mixture of ethyl acetate (10 ml) and cyclohexane (40 ml) to give the title compound as a white powder (0.31 g) m.p. 104°–104.5° TLC System A R$_f$ 0.62.

The following compounds were similarly prepared:

(b) 1-Methyl-$N^5$-[3-[3-(1-pyrrolidinylmethyl)phenoxy]propyl]-1H-1,2,4-triazole-3,5-diamine (4 g) gave 1-methyl-$N^5$-[3-[[5-(1-pyrrolidinylmethyl)-1,4-cyclohexadien-1-yl]oxy]propyl]-1H-1,2,4-triazole-3,5-diamine as a white powder (1.8 g), m.p. 84°–5°.

Assay found: C, 61.44; H, 8.43; N, 25.30; $C_{17}H_{28}N_6O$ requires: C, 61.34; H, 8.48; N, 24.92%.

(c) 1-Methyl-5-[[3-[3-(1-piperidinylmethyl)phenoxy]-propyl]amino]-1H-1,2,4-triazole-3-methanol (3.1 g) gave 1-methyl-5-[[3-[[5-(1-piperidinylmethyl)-1,4-cyclohexadien-1-yl]oxy]propyl]amino]-1H-1,2,4-triazole-3-methanol as a white powder (1.3 g), m.p. 122°–3°.

Assay found: C, 63.13; H, 8.64; N, 19.38; $C_{19}H_{31}N_5O_2$ requires: C, 63.12; H, 8.39; N, 19.34%.

(d) 1-Methyl-$N^5$-[3-[3-[(dimethyl)aminomethyl]phenoxy]propyl]-1H-1,2,4-triazole-3,5-diamine (1.0 g) gave 1-methyl-$N^5$-[3-[[5-[(dimethyl)aminomethyl]-1,4-cyclohexadien-1-yl]oxy]propyl-1H,1,2,4-triazole-3,5-diamine as a brown oil (0.1 g).

T.l.c. System A R$_f$ 0.6; N.m.r. (CDCl$_3$) 4.48, br.s, (1H); 5.4, br.s., (1H); 6.2,t, (2H); 6.5,s, (3H); 6.5,m, (2H); 7.2–7.4,m, (6H); 7.8,s, (6H); 8.0,m, (2H).

(e) 3-Phenylmethyl-$N^5$-[4-[3-(1-piperidinylmethyl)-phenoxy]butyl]-1H-1,2,4-triazole-5-amine (0.23 g) gave 3-phenylmethyl-$N^5$-[4-[1-[5-(1-piperidinylmethyl)cyclohexa-1,4-dienyl]oxy]butyl]-1H-1,2,4-triazole-5-amine as a white powder (0.06 g) m.p. 122°.

T.l.c. System B R$_f$ 0.6 N.m.r. (CDCl$_3$) 2.75,s, (5H); 4.35,s, (1H); 4.45,brs, (1H); 5.20,m, (1H); 5.45,brs, (1H); 6.12,s, (2H); 6.36,m, (2H); 6.8,m, (2H); 7.2–7.4, several s, (6H); 7.7,m, (4H); 8.2–8.8,m, (10H).

(f) 1-Methyl-$N^5$-[3-[4-(1-piperidinylmethyl)phenoxy]-propyl]-1H-1,2,4-triazole-3,5-diamine (0.92 g) gave 1-methyl-$N^5$-[3-[1-[4-(1-piperidinylmethyl)cyclohexa-1,4-dienyl]oxy]propyl]-1H-1,2,4-triazole-3,5-diamine as a white powder (0.10 g) m.p. 107°.

T.l.c. System B R$_f$ 0.6.

EXAMPLE 2

1-Methyl-$N^3$-(4-pyridinylmethylene)-$N^5$-[3-[[5-(1-pyrrolidinylmethyl)-1,4-cyclohexadien-1-yl]oxy]-propyl]-1H-1,2,4-triazole-3,5-diamine.

A stirred solution of 1-methyl-$N^5$-[3-[[5-(1-pyrrolidinylmethyl)-1,4-cyclohexadien-1-yl]oxy]propyl]-1H-1,2,4-triazole-3,5-diamine (0.95 g) and 4-pyridinecarboxaldehyde (0.35 g) in benzene (30 ml) was heated under reflux in a Dean-Stark separator for 30 h. The solution was evaporated in vacuo to give a solid which was recrystallised from ethyl acetate (10 ml) to afford the title compound as a yellow solid (0.35 g). m.p. 166°–167° C.

N.m.r. (CDCl$_3$) 0.86,s, (1H); 1.25,m, (2H); 2.2,m, (2H); 4.4,brs, (1H); 5.2,t, (1H); 5.4,brs, (1H); 6.1,t, (2H); 6.4,s+q, (5H); 7.0,s, (2H); 7.2,brs, (4H); 7.6,m, (4H); 8.0–8.2,m, (6H).

EXAMPLES OF PHARMACEUTICAL COMPOSITIONS

| Tablets | mg/tablet |
|---|---|
| Active ingredient | 100.00 |
| Microcrystalline Cellulose BPC | 198.50 |
| Magnesium stearate BP | 1.50 |
| Compression weight | 300.00 |

The active ingredient is sieved through a 250 μm sieve, blended with the excipients and compressed using 9.5 mm punches. Tablets of other strengths may be prepared by altering the compression weight and using punches to suit.

The tablets may be film coated with suitable film forming materials, e.g. methyl cellulose or hydroxypropyl methyl cellulose using standard techniques. Alternatively the tablets may be sugar coated.

| Injection for Intravenous Administration | % w/v |
|---|---|
| Active ingredient | 1.00 |
| Water for injections B.P. to | 100.00 |

Sodium chloride may be added to adjust the tonicity of the solution and the pH may be adjusted to that of maximum stability and/or to facilitate solution of the active ingredient using either dilute acid or alkali.

The solution is prepared, clarified and filled into appropriate sized ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen.

EXAMPLE 3

Following the method of Example 1, N-[5-[[3-[3-(1-Piperidinylmethyl)phenoxy]propyl]amino]-1-methyl-1H-1,2,4-triazol-3-yl]-acetamide (1.4 g) gave, after redissolving the crude product in ethyl acetate, washing with sodium carbonate, drying (MgSO$_4$) and evaporating the organic layer, N-[5-[[[3-[3-(1-piperidinylmethyl)cyclohexa-1,4-dienyl]oxy]propyl]amino]-1-methyl-1H-1,2,4-triazol-3-yl]-acetamide as a white powder (0.6 g). m.p. 51°–52°. T.l.c. system B Rf 0.7.

We claim:

1. A compound of the formula (I)

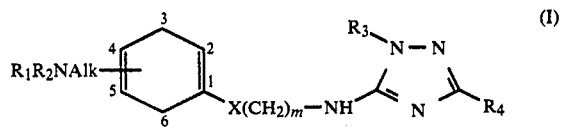

and physiologically acceptable salts and hydrates thereof in which $R_1$ and $R_2$, which may be the same or different, each represent hydrogen, $C_{1-10}$ alkyl, $C_{3-8}$ cycloalkyl, $C_{3-6}$ alkenyl, ar $C_{1-6}$ alkyl wherein ar is phenyl or phenyl substituted with one or more $C_{1-3}$ alkyl or $C_{1-3}$ alkoxy groups or halogen atoms; trifluoro $C_{1-6}$ alkyl, heteroaralkyl wherein the heteroaryl portion is furan or pyrrole and the alkyl portion is a straight or branched $C_{1-4}$ alkyl portion and the heteroaryl portion is linked to the alkyl portion through either a carbon or nitrogen atom; or $C_{1-6}$ alkyl substituted by hydroxy, $C_{1-6}$ alkoxy, amino, $C_{1-6}$ alkylamino, di $C_{1-6}$ alkylamino or $C_{3-8}$ cycloalkyl, or $R_1$ and $R_2$ may together with the nitrogen atom to which they are attached form a pyrrolidino, piperidino, hexamethylenimino, heptamethyleneimino, tetrahydropyridino, 4-hydroxypiperidino, 4-$C_{1-3}$ alkylpiperidino, morpholino, 2,6-di-$C_{1-3}$ alkylmorpholino or thiomorpholino group; Alk represents a straight or branched alkylene chain of 1 to 6 carbon atoms and is attached to the cyclohexadiene ring at the 4- or 5-position; X represents —CH$_2$ or —O—; m represents 2, 3, 4 or 5 and when X is —O— the chain (CH$_2$)$_m$ may be interrupted by an oxygen atom provided that there are at least two methylene groups between any two heteroatoms in the moiety —X(CH$_2$)$_m$NH—; $R_3$ represents hydrogen, $C_{1-6}$ alkyl, $C_{3-6}$ alkenyl, ar $C_{1-6}$ alkyl wherein ar is phenyl or phenyl substituted with one or more $C_{1-3}$ alkyl groups or $C_{1-3}$ alkoxy groups or halogen atoms; or $C_{2-6}$ alkyl substituted by hydroxy or $C_{1-6}$ alkoxy; and $R_4$ represents hydrogen, $C_{1-6}$ alkyl, $C_{3-6}$ alkenyl, ar $C_{1-6}$ alkyl wherein the ar portion is phenyl or phenyl substituted by one or more $C_{1-3}$ alkyl or $C_{1-3}$ alkoxy groups or halogen atoms; hydroxy $C_{1-6}$ alkyl, acyloxy $C_{1-6}$ alkyl wherein the acyl portion is benzoyl or benzoyl substituted with one or more $C_{1-3}$ alkyl or $C_{1-3}$ alkoxy groups or halogen atoms, ar $C_{1-6}$ alkanoyl wherein ar is phenyl or phenyl substituted with one or more $C_{1-3}$ alkyl or $C_{1-3}$ alkoxy groups or halogen atoms, or $C_{1-6}$ alkanoyl; $C_{1-6}$ alkoxy $C_{1-6}$ alkyl, aryloxy $C_{1-6}$ alkyl wherein the aryl portion is phenyl or phenyl substituted with one or more $C_{1-3}$ alkyl or $C_{1-3}$ alkoxy groups or halogen atoms; ar $C_{1-6}$ alkyloxy $C_{1-6}$ alkyl wherein the aryl portion is phenyl or phenyl substituted with one or more $C_{1-3}$ alkyl or $C_{1-3}$ alkoxy groups or halogen atoms; amino $C_{1-6}$ alkyl, $C_{1-6}$ alkyl amino $C_{1-6}$ alkyl, di $C_{1-6}$ alkylamino $C_{1-6}$ alkyl, hydroxy or $C_{1-6}$ alkoxy or the group NR$_5$R$_6$ where R$_5$ represents hydrogen, $C_{1-6}$ alkyl, $C_{1-6}$ alkyl substituted by hydroxy or $C_{1-3}$ alkoxy, $C_{3-6}$ alkenyl, ar $C_{1-6}$ alkyl wherein the aryl portion is phenyl or phenyl substituted with one or more $C_{1-3}$ alkyl or $C_{1-3}$ alkoxy groups or halogen atoms; or heteroar $C_{1-6}$ alkyl wherein the heteroaryl portion is furyl, pyridyl, thiazolyl or thienyl; and R$_6$ represents any of the groups defined for R$_5$ or may represent the group COR$_7$ where R$_7$ represents hydrogen, $C_{1-6}$ alkyl, phenyl or phenyl substituted with one or more $C_{1-3}$ alkyl or $C_{1-3}$ alkoxy groups or halogen atoms; ar $C_{1-6}$ alkyl wherein ar is phenyl or phenyl substituted with one or more $C_{1-3}$ alkyl or $C_{1-3}$ alkoxy groups or halogen atoms; $C_{1-6}$ alkoxy, furyl, pyridyl, thiazolyl or thienyl group, or monocyclic heteroar $C_{1-6}$ alkyl wherein the heteroaryl portion is furyl, pyridyl, thiazolyl or thienyl; or R$_6$ represents the group SO$_2$R$_8$ where R$_8$ represents $C_{1-6}$ alkyl or phenyl or phenyl substituted by one or more $C_{1-3}$ alkyl or $C_{1-3}$ alkoxy groups or halogen atoms; or R$_6$ represents the group

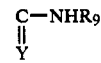

where Y is oxygen or sulphur and R$_9$ represents hydrogen, $C_{1-6}$ alkyl, $C_{3-8}$ cycloalkyl, phenyl or phenyl substituted with one or more $C_{1-3}$ alkyl or $C_{1-3}$ alkoxy groups or halogen atoms; or ar $C_{1-6}$ alkyl wherein the aryl portion is phenyl or phenyl substituted with one or more $C_{1-3}$ alkyl or $C_{1-3}$ alkoxy groups or halogen atoms; or R$_5$ and R$_6$ taken together may represent the group =CR$_{10}$R$_{11}$ where R$_{10}$ represents phenyl or phenyl substituted with one or more $C_{1-3}$ alkyl or $C_{1-3}$ alkoxy groups or halogen atoms or furyl, pyridyl, thiazolyl or thienyl group; and R$_{11}$ represents hydrogen or $C_{1-6}$ alkyl.

2. A compound according to claim 1 in which the groups R$_1$ to R$_4$ have the following meanings:

R$_1$: $C_{1-6}$ alkyl, $C_{5-7}$ cycloalkyl, $C_{3-6}$ alkenyl, ar $C_{1-6}$ alkyl wherein ar is phenyl or phenyl substituted with one or more $C_{1-3}$ alkyl or $C_{1-3}$ alkoxy groups or halogen atoms; $C_{1-4}$ alkyl substituted by a trifluoromethyl group, hydroxy $C_{2-4}$ alkyl, $C_{1-3}$ alkoxy $C_{2-4}$ alkyl, or di-$C_{1-3}$ alkylamino $C_{1-4}$ alkyl;

$R_2$: hydrogen or $C_{1-4}$ alkyl; or $R_1R_2N$ may represent a pyrrolidino, piperidino, hexamethylenimino, heptamethyleneimino, tetrahydropyridino, 4-hydroxypiperidino, 4-$C_{1-3}$ alkylpiperidino, morpholino, 2,6-di-$C_{1-3}$ alkylmorpholino or thiomorpholino group;

$R_3$: hydrogen, $C_{1-4}$ alkyl, or hydroxy $C_{2-4}$ alkyl;

$R_4$: hydrogen, hydroxy, $C_{1-4}$ alkyl, hydroxy $C_{1-4}$ alkyl, $C_{1-3}$ alkoxy $C_{1-4}$ alkyl, phenyl $C_{1-3}$ alkyl, $C_{2-4}$ alkanoyloxy $C_{1-4}$ alkyl, amino $C_{1-4}$ alkyl, amino, $C_{1-4}$ alkylamino, di-$C_{1-4}$ alkylamino, phenyl $C_{1-3}$ alkylamino or a heteroaryl $C_{1-3}$ alkylamino group where the heteroaryl ring is furyl, pyridyl, thiazolyl or thienyl; or the group $NHCOR_7$ where $R_7$ represents hydrogen, $C_{1-3}$ alkyl, $C_{1-3}$ alkoxy, furyl, pyridyl, thiazolyl, thienyl, or phenyl optionally substituted by a $C_{1-3}$ alkyl or $C_{1-3}$ alkoxy group; or the group $NHSO_2R_8$ where $R_8$ represents $C_{1-3}$ alkyl or phenyl optionally substituted by a $C_{1-3}$ alkyl or $C_{1-3}$ alkoxy group; or the group $NHCONHR_9$ where $R_9$ is $C_{1-3}$ alkyl, $C_{5-7}$ cycloalkyl, or phenyl optionally substituted by a $C_{1-3}$ alkyl or $C_{1-3}$ alkoxy group; or the group $N=CHR_{10}$ where $R_{10}$ is a phenyl or pyridyl group; and the group Alk is the group $(CH_2)_n$ where n is 1, 2 or 3.

3. A compound according to claim 1 corresponding to formula (II)

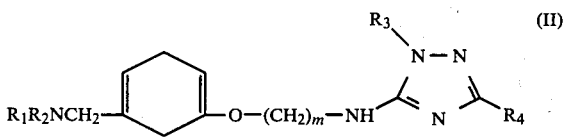

where $R_1$ and $R_2$ are methyl groups or together with the nitrogen atom to which they are attached form a pyrrolidino, piperidino or hexamethylenimino group; m is 3 or 4, $R_3$ is hydrogen or methyl; and $R_4$ is an amino, hydroxy $C_{1-6}$ alkyl, $C_{1-6}$ alkanoyloxy $C_{1-6}$ alkyl, $C_{1-6}$ alkoxy $C_{1-6}$ alkyl, amino $C_{1-6}$ alkyl, benzyl, formamido, $C_{1-6}$ alkoxycarbonylamino, hydroxy, aroylamino wherein the aroyl portion is benzoyl or benzoyl substituted by one or more $C_{1-3}$ alkyl or $C_{1-3}$ alkoxy groups or halogen atoms; or a phenylcarbamoylamino group.

4. A compound according to claim 1 in which m represents 2, 3 or 4 and $R_4$ represents hydrogen, $C_{1-6}$ alkyl, $C_{3-6}$ alkenyl, ar $C_{1-6}$ alkyl wherein the aryl portion is phenyl or phenyl substituted with one or more $C_{1-3}$ alkyl or $C_{1-3}$ alkoxy groups or halogen atoms; hydroxy $C_{1-6}$ alkyl, $C_{1-6}$ alkoxy $C_{1-6}$ alkyl, hydroxy or $C_{1-6}$ alkoxy or the group $NR_5R_6$ where $R_5$ represents hydrogen, $C_{1-6}$ alkyl, hydroxy $C_{1-6}$ alkyl, $C_{3-6}$ alkenyl, or ar $C_{1-6}$ alkyl wherein the aryl portion substituted by hydroxy or $C_{1-6}$ alkoxy; and $R_4$ represents hydrogen, $C_{1-6}$ alkyl, $C_{3-6}$ alkenyl, ar $C_{1-6}$ alkyl wherein the ar portion is phenyl or phenyl substituted by one or more $C_{1-3}$ alkyl or $C_{1-3}$ alkoxy groups or halogen atoms; hydroxy $C_{1-6}$ alkyl, acyloxy $C_{1-6}$ alkyl wherein the acyl portion is benzoyl or benzoyl substituted with one or more $C_{1-3}$ alkyl or $C_{1-3}$ alkoxy groups or halogen atoms, ar $C_{1-6}$ alkanoyl wherein ar is phenyl or phenyl substituted with one or more $C_{1-3}$ alkyl or $C_{1-3}$ alkoxy groups or halogen atoms, or $C_{1-6}$ alkanoyl; $C_{1-6}$ alkoxy $C_{1-6}$ alkyl, aryloxy $C_{1-6}$ alkyl wherein the aryl portion is phenyl or phenyl substituted with one or more $C_{1-3}$ alkyl or $C_{1-3}$ alkoxy groups or halogen atoms; ar $C_{1-6}$ alkyloxy $C_{1-6}$ alkyl wherein the aryl portion is phenyl or phenyl substituted with one or more $C_{1-3}$ alkyl or $C_{1-3}$ alkoxy groups or halogen atoms; amino $C_{1-6}$ alkyl, $C_{1-6}$ alkyl amino $C_{1-6}$ alkyl, di $C_{1-6}$ alkylamino $C_{1-6}$ alkyl, hydroxy or $C_{1-6}$ alkoxy or the group $NR_5R_6$ where $R_5$ represents hydrogen, $C_{1-6}$ alkyl, $C_{1-6}$ alkyl substituted by hydroxy or $C_{1-3}$ alkoxy, $C_{3-6}$ alkenyl, ar $C_{1-6}$ alkyl wherein the aryl portion is phenyl or phenyl substituted with one or more $C_{1-3}$ alkyl or $C_{1-3}$ alkoxy groups or halogen atoms; or heteroar $C_{1-6}$ alkyl wherein the heteroaryl portion is furyl, pyridyl, thiazolyl or thienyl; and $R_6$ represents any of the groups defined for $R_5$ or may is phenyl or phenyl substituted with one or more $C_{1-3}$ alkyl or $C_{1-3}$ alkoxy groups or halogen atoms; and $R_6$ represents hydrogen, $C_{1-6}$ alkyl or hydroxy $C_{1-6}$ alkyl, or $COR_7$ where $R_7$ represents hydrogen, $C_{1-6}$ alkyl, phenyl or phenyl substituted with one or more $C_{1-3}$ alkyl or $C_{1-3}$ alkoxy groups or halogen atoms; ar $C_{1-6}$ alkyl wherein the aryl portion is phenyl or phenyl substituted with one or more $C_{1-3}$ alkyl or $C_{1-3}$ alkoxy groups or halogen atoms; or $C_{1-6}$ alkoxy, or $R_6$ represents the group $SO_2R_8$ where $R_8$ represents $C_{1-6}$ alkyl or phenyl or phenyl substituted with one or more $C_{1-3}$ alkyl or $C_{1-3}$ alkoxy groups or halogen atoms; or $R_5$ and $R_6$ together represent the group $=CR_{10}R_{11}$ where $R_{10}$ represents phenyl or phenyl substituted with one or more $C_{1-3}$ alkyl or $C_{1-3}$ alkoxy groups or halogen atoms or furyl, pyridyl, thiazolyl or thienyl; and $R_{11}$ represents hydrogen or $C_{1-6}$ alkyl.

5. A compound according to claim 1 in which the group $R_1R_2NAlk$ is attached at the 5-position of the cyclohexadiene ring, X is oxygen and m is 3 or 4.

6. A compound according to claim 5 corresponding to formula (II)

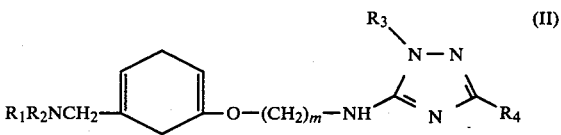

where $R_1$ and $R_2$ are methyl groups or together with the nitrogen atom to which they are attached form a pyrrolidino, piperidino or hexamethylenimino group; m is 3 or 4, $R_3$ is hydrogen or methyl; and $R_4$ represents amino, $C_{1-6}$ alkanoylamino, hydroxy $C_{1-6}$ alkyl, benzyl or pyridylmethylenamino.

7. A compound according to claim 1 which is:
1-methyl-$N^5$-[3-[[5-(1-piperidinylmethyl)-1,4-cyclohexadien-1-yl]oxy]propyl]-1H-1,2,4-triazole-3,5-diamine; and 1-methyl-5-[[3-[[5-(1-piperidinylmethyl)-1,4-cyclohexadien-1-yl]oxy]propyl]amino]-1H-1,2,4-triazole-3-methanol and their physiologically acceptable salts.

8. A pharmaceutical composition for the treatment of conditions mediated through $H_2$-receptors comprising an effective amount of at least one compound as claimed in claim 1 together with at least one pharmaceutically acceptable carrier or diluent.

9. A method of treating a condition mediated through histamine $H_2$-receptors which comprises administering to a patient an effective amount of a compound according to claim 1 to relieve said condition.

* * * * *